United States Patent [19]

Bridger

[11] 4,162,224

[45] Jul. 24, 1979

[54] SOLUBILIZED BORATES OF BIS-OXAZOLINE AND LUBRICANT COMPOSITIONS CONTAINING THE SAME

[75] Inventor: Robert F. Bridger, Hopewell, N.J.

[73] Assignee: Mobil Oil Corporation, New York, N.Y.

[21] Appl. No.: 763,736

[22] Filed: Jan. 28, 1977

[51] Int. Cl.$^2$ .................... C10M 1/10; C10M 1/54; C10M 5/28
[52] U.S. Cl. ............................ 252/49.6; 260/307 R; 260/307 A; 252/46.3
[58] Field of Search ............................ 252/49.6, 46.3; 260/244 R, 246 R, 307 R, 307 A

[56] References Cited

U.S. PATENT DOCUMENTS

| | | | |
|---|---|---|---|
| 3,389,124 | 6/1968 | Sparks | 252/49.6 X |
| 3,446,808 | 5/1969 | Cyba | 252/49.6 X |
| 3,505,226 | 4/1970 | Cyba | 252/49.6 |
| 4,035,309 | 7/1977 | Brois | 252/49.6 UX |

FOREIGN PATENT DOCUMENTS 1444904  2/1969  Fed. Rep. of Germany ... 252/49.6 UX

*Primary Examiner*—Paul F. Shaver
*Attorney, Agent, or Firm*—Charles A. Huggett; Raymond W. Barclay; Howard M. Fluornoy

[57] ABSTRACT

Novel oil-soluble compounds and lubricating compositions containing them are provided containing an antiwear or antioxidant improving amount of a solubilized borate of a bis-oxazoline resulting from reaction of an alkyloxazoline, boric acid and a substituted phenol.

14 Claims, No Drawings

SOLUBILIZED BORATES OF BIS-OXAZOLINE AND LUBRICANT COMPOSITIONS CONTAINING THE SAME

BACKGROUND OF THE INVENTION

1. Field of the Invention

This invention relates to new compounds useful as antiwear and/or antioxidant additives and to lubricant compositions, such as lubricating oils, automotive oils, gear oils, transmission fluids, greases and similar lubricants normally improved by the presence therein of antiwear and/or antioxidant additives.

2. Description of the Prior Art

The metal surfaces of machinery or engines operating under heavy loads wherein metal slides against metal may undergo excessive wear or corrosion. Often, the lubricants used to protect the metal surfaces deteriorate under such heavy loads and as a result, do not prevent wear at the points of metal to metal contact. Consequently, the performance of the machine or engine will suffer, and in aggravated cases the machine or engine may become completely inoperative.

It is also known that lubricants are prone to oxidative deterioration when subjected to elevated temperatures or even when they are exposed to atmospheric conditions for long periods of time. Such deterioration of lubricants, including lubricating oils and greases, produces loss of lubricating properties of the oil, grease or other lubricant subjected to oxidation.

There have been many attempts to devise additive systems which would provide satisfactory protection in imparting desired antiwear and antioxidant properties to the lubricant used under the above conditions. Many prior art additives have been only marginally effective in accomplishing such objective except at unacceptably high concentrations, especially when the lubricants are subjected to drastic oxidizing conditions.

U.S. Pat. No. 3,682,935 describes certain heterocyclic aromatic oxygen-boron-nitrogen compounds useful as antioxidants in organic media. U.S. Pat. No. 3,437,596 describes specified boroxarophenanthreneamine compounds as antioxidants and U.S. Pat. No. 3,361,672 describes certain aromatic cyclic dioxaboron compounds as being useful in stabilizing organic compositions against oxidative deterioration.

SUMMARY OF THE INVENTION

In accordance with the present invention, it has been found that certain novel borates of bis-oxazolines are excellent antiwear and antioxidant additive compounds and that lubricant compositions containing the same are substantially improved with respect to antiwear and antioxidant properties.

The novel compounds of this invention are prepared by the reaction of a bis-oxazoline, boric acid and a substituted phenol, preferably a hindered phenol. If the latter reactant is omitted, the resulting compositions, as will be evident from data presented hereinafter, are oil-insoluble. Reaction is suitably effected at a temperature between about 60° and about 180° C. employing a molar ratio of bis-oxazoline:boric acid:substituted phenol between about 1:1:1 and about 1:3:5.

The bis-oxazoline or oxazoline reactants employed herein are characterized by the general formulae:

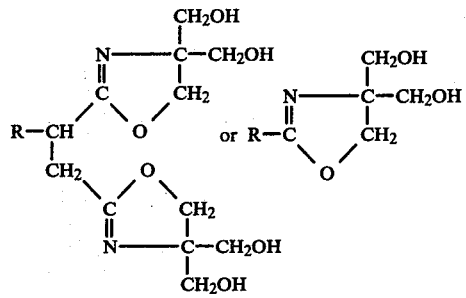

where R is a straight chain, branched chain or cycloalkyl group containing from 4 to 30 carbon atoms. Typical alkyl substituents include butyl, pentyl, hexyl, octyl, eicosyl, cyclohexyl, cyclopentyl and other cycloalkyl such as in the oxazoline derived from a mixture of napthenic acids. These compounds can be prepared by available methods, such as reaction of the appropriate alkyl substituted succinic anhydride and tris(hydroxymethyl)aminomethane. Thus, n-$C_{18}$-bis oxazoline may be synthesized by reaction of n-octadecylsuccinic anhydride and tris(hydroxymethyl) aminomethane.

In addition to or in place of boric acid, it is contemplated that other suitable boron compounds may be used including by way of example trialkyl borates, such as trimethyl borate, triethyl borate or tributyl borate; boron trichloride and borane.

The substituted phenols used herein include hydroyaryl compounds of the general structures:

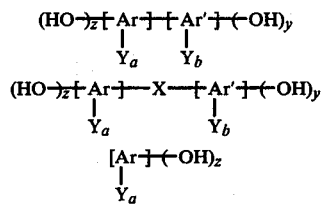

wherein X may be alkylene group having from 1 to 5 carbon atoms, such as methylene or 2,2-propylene; oxygen or sulfur and y and z may each be 1 or 2. Ar and Ar' may be each phenyl, naphthyl, or anthracenyl and have $Y_a$ and $Y_b$ substituents such as alkyl, aryl or non-hydrocarbyl substituents. Preferred are the hindered phenols having the latter substituents in position adjacent to the hydroxy group, it being understood that similar type substituents may also occupy positions on the aromatic ring other than in a position adjacent to the hydroxy group. These substituted phenols or bisphenols are prepared by methods well known in the art. Preferred substituents are alkyl or substituted alkyl radicals of from 1 to 20 carbon atoms, occupying from 1 to 4 available positions on the nucleus. Tertiary alkyl-substituted compounds, such as 2,6-ditertiary butylphenols or substituted derivatives thereof are preferred. Typical of such reactants are 2,6-di-tert-butylphenol, 2,6-di-tert-butyl-4-methylphenol, 2,6-di-tert-butyl-4-hydroxymethylphenol, 4,4'-methylenebis(2,6-di-tert-butylphenol) and 4,4'-thiobis(2,6-di-tert-butylphenol).

The solubilized borates of bis-oxazolines described herein can be effectively employed in any amount which is sufficient for imparting the desired degree of antiwear and/or antioxidant protection. In many instances, the oil-soluble borate of bis-oxazoline is effectively employed in an amount from about 0.001 to about 10 percent by weight and preferably in an amount from about 0.1 to about 5 percent by weight of the total weight of the lubricant composition.

The above-described bis-oxazoline borate antiwear and/or antioxidant improving agents may be incorporated in any lubricating media which may comprise oils, e.g., mineral oil or synthetic oils; or greases in which any of the aforementioned oils are employed as a vehicle. In generaly, mineral oils, employed as the lubricant, or grease vehicle may be of any suitable lubricating viscosity range, as, for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

As hereinbefore indicated, the aforementioned additives may be incorporated as antiwear agents in grease compositions. Such oils can also include hydraulic oils, if so desired. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above-described additives, are combined with a grease-forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickners, such as surface-modified clays and silicas, aryl ureas, calcium complexes and similar materials. In general, grease thickners may be employed which do not melt and dissolve when used at the required temperature within a particular environment; however, in all other respects, any material which is normally employed for thickening or gelling hydrocarbon fluids or forming greases can be used in preparing the aforementioned improved greases in accordance with the present invention.

DESCRIPTION OF SPECIFIC EMBODIMENTS

The following examples will serve to illustrate the additives and lubricant compositions of the invention without limiting the same.

EXAMPLE 1 n-$C_{18}$-Bis-oxazoline (19.98 grams, 0.037 mol) and boric acid (2.29 grams, 0.037 mol) were refluxed in 100 ml toluene for 3 hours, 10 minutes, while collecting the azeotroped water of reaction (1.6 ml, 0.089 mol) in a Dean-Stark trap. Upon cooling, the reaction mixture was filtered through a medium (15 microns) fritted glass filter, and solvent was removed by distillation under reduced pressure to yield 18.8 grams (90% yield) of product containing 1.8% boron.

EXAMPLE 2 n-$C_{18}$-Bis-oxazoline (19.98 grams, 0.037 mol) and boric acid (4.57 grams, 0.074 mol) were refluxed in 100 ml toluene for 2.5 hours, while collecting the azeotroped water of reaction (2.60 ml, 0.14 mol) in a Dean-Stark trap. Upon cooling, the reaction mixture was filtered through a medium fritted glass filter, and solvent was removed by distillation under reduced pressure to yield 17.8 grams (81.3% yield) of product containing 3.5% boron.

EXAMPLE 3 n-$C_{18}$-Bis-oxazoline (19.98 grams, 0.037 mol), boric acid (4.57 grams, 0.074 mol), and 2,6-di-tert-butyl-4-methylphenol (16.28 grams, 0.074 mol) were refluxed in 100 ml toluene for 118 hours, while collecting the azeotroped water of reaction (3.5 ml, 0.19 mol) in a Dean-Stark trap. Upon cooling the reaction mixture was filtered through a medium fritted glass filter, and solvent was removed by distillation at reduced pressure to yield 32.6 grams (89% yield) of product containing 2.1% boron.

EXAMPLE 4 n-$C_{18}$-Bis-oxazoline (19.98 grams, 0.037 mol), boric acid (4.57 grams, 0.074 mol), and 2,6-di-tert-butyl-4-hydroxylmethylphenol (17.46 grams, 0.074 mol) were refluxed in 200 ml toluene for 22 hours, while collecting the azeotroped water of reaction (4 ml, 0.22 mol) in a Dean-Stark trap. Upon cooling, the reaction mixture was filtered through a medium fritted glass filter, and solvent was removed by distillation at reduced pressure to yield 36.2 grams (95% yield) of product containing 1.8% boron.

Application of the products of Examples 3 and 4, illustrative of the invention, is shown below in terms of improved solubility in lubricating oil as compared with the products of Examples 1 and 2 wherein the hindered phenol reactant was omitted.

Thus, the products from Examples 1 through 4 were tested for solubility by stirring in a 150 SUS solvent-refined mineral oil at 130° C. for 30 minutes with the following result:

| Example | Solubility, g/100 g oil |
|---|---|
| 1 | 0.1 (insoluble) |
| 2 | 0.1 (insoluble) |
| 3 | 2 (soluble) |
| 4 | 2 (soluble) |

It will be seen that the products of Examples 1 and 2 were insoluble in mineral oil, whereas the inclusion of hindered phenols in the preparation of the products from Examples 3 and 4 resulted in soluble products.

Applicability of the compounds of the present invention as antioxidants is shown by an oxygen absorption test. In accordance with this test, oxidations were conducted in an oxygen circulation apparatus of the type described by Dornte in Ind. Engr. Chem., Vol. 28, Page 26 (1936), modified so the rate of oxygen absorption could be recorded automatically. A 30 gram test sample of a 0.5 weight percent concentration of the compound in hexadecane was placed in a 28×260 mm tube and permitted to equilibrate thermally before the oxygen flow was begun. Oxygen was then introduced to the sample at a rate of 5 liters/hour through a fritted glass disk 3mm from the bottom of the tube. The inhibition period, $t_{1.0}$, was taken as the time required for the absorption of 1 mol of oxygen per kilogram of the sample. It will be evident that the larger the value of $t_{1.0}$, the more effective is the additive as an antioxidant. The products of Examples 2 and 3 were evaluated by the above method as antioxidants at a temperature of 175° C., the products of Examples 1 and 2 not being sufficiently soluble to test. Results are shown in the table below:

| Additive | $t_{1.0}$, Hours |
|---|---|
| None (Hexadecane only) | 1.1 |
| Example 3, (0.5 wt. % in hexadecane) | 21.9 |
| Example 4 (0.5 wt. % in hexadecane) | 30.2 |

The additives of Examples 3 and 4, illustrative of the invention, were tested for antiwear activity using the Four Ball Wear Test described in U.S. Pat. No. 3,423,316. In general, in this test, three steel balls are held in a ball cup. A fourth ball positioned on a rotatable vertical axis is brought into contact with the three balls and is rotated against them. The force with which the fourth ball is held against the three stationary balls may be varied according to a desired load. The test lubricant is added to the ball cup and acts as a lubricant for the rotation. At the end of the test, the steel balls are investigated for wear scar, the extent of scarring represents the effectiveness of the lubricant for antiwear. Results are also reported as wear rates in volume of wear per unit sliding distance per kilogram load. The lower the wear rate, the more effective is the lubricant for antiwear. The base stock oil employed in accordance with the test results shown in the table below was a 150 SSU at 210° F. solvent-refined paraffinic bright stock lubricating oil. Standard conditions of 40 kilograms load, 600 RPM and 30 minutes test time were employed at 200° F.

| Additive | Wear Scar Diameter, mm | Wear Rate × $10^{12}$ cc/cm-Kg |
|---|---|---|
| None (Base Oil Only) | 0.6858 | 4.60 |
| Example 3 (2 Wt. % in Base Oil) | 0.4775 | 0.89 |
| Example 4 (2 Wt. % in Base Oil) | 0.4890 | 1.00 |

As will be evident from the above data, the inclusion of a small amount in a mineral base oil of the additive of this invention served to very substantially improve the antiwear characteristics thereof.

I claim:

1. A lubricant composition comprising a major proportion of a base oil of lubricating viscosity or greases thereof containing a minor amount, sufficient to improve the antioxidant or antiwear properties thereof, of the product obtained by reaction at a temperature between about 60° and about 180° C. of (A) a bis-oxazoline or oxazoline reactant characterized by the general formula:

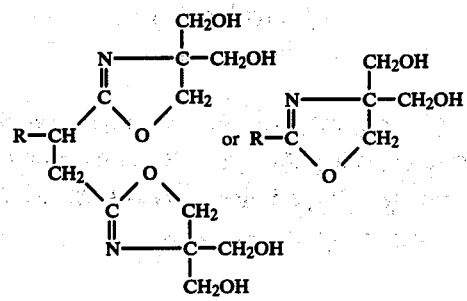

where R is a straight chain, branched chain or cycloalkyl group containing from 4 to 30 carbon atoms, (B) boric acid and (C) a substituted phenol selected from those having the general structures:

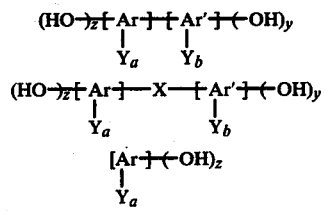

wherein X is an alkylene group having from 1 to 5 carbon atoms; oxygen or sulfur; y and z are either 1 or 2; Ar and Ar' are phenyl, naphthyl or anthracenyl and $Y_a$ and $Y_b$ are substituents selected from alkyl, aryl or non-hydrocarbyl substituents; the molar ratio of A:B:C being between about 1:1:1 and about 1:3:5.

2. The composition of claim 1 wherein the amount of said product present is between about 0.001 and about 10 percent by weight.

3. The composition of claim 1 wherein the amount of said product present is between about 0.1 and about 5 percent by weight.

4. The composition of claim 1 wherein said base oil is a mineral oil.

5. The composition of claim 1 wherein said base oil is a synthetic oil.

6. The composition of claim 1 wherein reactant (A) is n-$C_{18}$-bis oxazoline.

7. The composition of claim 1 wherein $Y_a$ and $Y_b$ substituents are alkyl or substituted alkyl radicals of from 1 to 20 carbon atoms.

8. The composition of claim 1 wherein reactant (C) is a ditertiary alkyl-substituted phenol.

9. The composition of claim 1 wherein reactant (C) is 2,6-ditertiary butylphenol or substituted derivative thereof.

10. A solubilized borate of a bis-oxazoline resulting from reaction at a temperature between about 60° and about 180° C. of (A) a bis-oxazoline or oxazoline reactant characterized by the general formula:

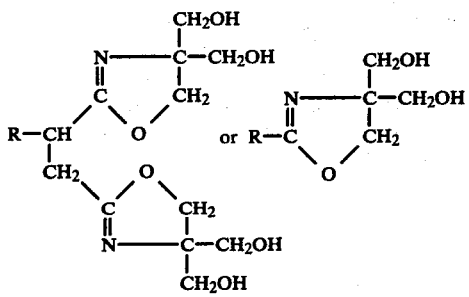

where R is a straight chain, branched chain or cycloalkyl group containing from 4 to 30 carbon stoms, (B) boric acid and (C) a substituted phenol selected from those having the general structures:

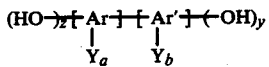

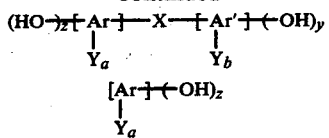

wherein X is an alkylene group having from 1 to 5 carbon atoms; oxygen or sulfur; y and z are either 1 or 2; Ar and Ar' are phenyl, naphthyl or anthracenyl and $Y_a$ and $Y_b$ are substituents selected from alkyl, aryl or non-hydrocarbyl substitutents; the molar ratio of A:B:C being between about 1:1:1 and about 1:3:5.

11. The borate of claim 10 wherein reactant (A) is n-$C_{18}$-bis-oxazoline.

12. The borate of claim 10 wherein $Y_a$ and $Y_b$ substituents are alkyl or substituted alkyl radicals of from 1 to 20 carbon atoms.

13. The borate of claim 10 wherein reactant (C) is a ditertiary alkyl-substituted phenol.

14. The borate of claim 10 wherein reactant (C) is 2,6-ditertiary butylphenol or substituted derivatives thereof.

* * * * *